United States Patent [19]

Mackles

[11] Patent Number: 4,639,367
[45] Date of Patent: Jan. 27, 1987

[54] AEROSOL FOAM

[75] Inventor: Leonard Mackles, New York, N.Y.

[73] Assignee: Product Resources International, Inc., New York, N.Y.

[21] Appl. No.: 778,026

[22] Filed: Sep. 20, 1985

Related U.S. Application Data

[63] Continuation-in-part of Ser. No. 713,294, Mar. 18, 1985, abandoned.

[51] Int. Cl.$^4$ .............................................. A61K 9/00
[52] U.S. Cl. ...................................... 424/45; 514/945
[58] Field of Search ............................................ 424/45

[56] References Cited

U.S. PATENT DOCUMENTS 4,174,295  11/1979  Bargigia et al. ...................... 252/305
4,425,164  1/1984  Bliznak et al. ...................... 106/150

Primary Examiner—Leonard Schenkman
Attorney, Agent, or Firm—Amster, Rothstein & Ebenstein

[57] ABSTRACT

A stable, edible anhydrous aerosol foam capable of suspending up to 50% by weight of dispersed solid particles is prepared using a foamable liquid oil, a foaming agent and a food grade propellant. The foam is a stable whip having the consistency of whipped cream and can be dispensed in repeatable and measurable doses onto a spoon. It is useful to dispense a wide variety of therapeutic agents and, in particular, as an alternative to tablets which are hard to swallow or liquid medicines having a bad taste.

23 Claims, No Drawings

AEROSOL FOAM

This application is a continuation-in-part of U.S. patent application Ser. No. 713,294, filed Mar. 18, 1985 now abandoned.

BACKGROUND OF THE INVENTION

Tablets and capsules are the most common dosage forms for the oral administration of nutritional, medicinal, or other therapeutic products. It is well-known, however, that these dosage forms are unacceptable for use by people who have difficulty in swallowing tablets and capsules and that the difficulty is exacerbated by larger tablets and capsules and, in some instances, by the bad taste of the medication. It is generally accepted that these types of problems with medications are serious because they may lead to a failure on the part of patients to comply with the medication regimen ordered by the physician.

The common alternatives to conventional tablets and capsules are chewable tablets and aqueous or hydroalcoholic liquids such as syrups, suspensions and elixirs. Such dosage forms are commonly used for antacids, analgesics, cough and cold medications, antibiotics, vitamins and many other nutritional or medicinal products. In general, these forms do not significantly improve the taste of a medication or make it easier to swallow larger doses. For example, antacids in either chewable tablet or aqueous suspension form are generally disliked because they are gritty, astringent and leave an unpleasant aftertaste.

Although aerosol packaging has found high consumer acceptance in many areas, including pharmaceutical products such as inhalants, it has not heretofore been considered for use in formulations requiring a high concentration of suspended solids, i.e., greater than 5 to 13%, because a high solids content usually causes malfunctioning of the aerosol valve. It is neither economical nor practical to dispense therapeutic agents in the very dilute formulations which would be required for dispensing through an aerosol valve. Moreover, such dilute formulations usually produce an uncontrollable and unmeasurable spray, thereby making it difficult to control or measure the amount of the formulation being dispensed. A further difficulty with aerosol packaging is that most aqueous aerosol solutions would be unacceptable for dispensing medications because the dissolution of the active ingredient prior to ingestion could reduce its bioavailability and also produce an unpleasant taste.

There are several prior art patents which disclose anhydrous aerosol foams. For example, U.S. Pat. No. 3,770,648 discloses an anhydrous aerosol foam composition for external use which incorporates a silicone resin in a solution of organic solvents to produce a stable "quick breaking" foam when the foam is rubbed into or spread over a surface on which it has been deposited. The '648 patent does not disclose any anhydrous foam products which are suitable for ingestion. It also does not teach any type of dosable or meterable foam for dispensing high concentrations of solid therapeutic agents.

U.S. Pat. No. 3,849,580 discloses an aerosol dispensing system which delivers non-aqueous butter-like edible fat compositions in a foam form. These foams contain no foaming agent and are intended to be used as food spreads.

U.S. Pat. No. 4,425,164 teaches the preparation of an aerosol spray cookware lubricant composition similar to the product which is commercially available in food stores under the trademark "PAM". This spray is formed from a mixture of a vegetable oil solution of an emulsifier (lecithin) in admixture with at least 10%, preferably 20 to 30%, of a hydrocarbon propellant and up to 15%, preferably 3 to 10%, of suspended flour or starch particles. The resulting product is a spray in which the particles serve as a visual indicator that the spray is being uniformly applied to the cooking surface. There is no disclosure or suggestion of a directly ingestible stable foam product capable of yielding repeatable, measurable doses of an active, solid therapeutic agent from an aerosol container.

Other disclosures of vegetable oil, lecithin-containing edible aerosols (U.S. Pat. No. 4,188,412 and 3,821,007) also indicate that such materials are sprays rather than foams. These patents additionally teach that foaming action would be undesirable in such a product.

SUMMARY OF THE DISCLOSURE

It has now been found that a stable, edible, anhydrous aerosol foam or whip capable of suspending up to 50% by weight of a dispersed solid can be prepared from a foamable, edible anhydrous liquid oil; a foaming agent; and controlled amounts of a food grade propellant which are sufficient to produce a stable foam rather than a spray. The foam, as delivered from an aerosol canister, has the consistency of whipped cream, is stable for extended periods and is hostile to the growth of micro-organisms so that refrigeration is not required. It can be safely ingested so that it is ideal as a carrier for medicines, vitamins, minerals or other solid therapeutic agents. Additionally, since most drugs are not soluble in the ingredients of the foam, a drug incorporated therein is kept out of solution in the mouth. Thus, the foam of this invention assists in masking the taste of bitter water-soluble drugs such as acetaminophen, smoothing the taste of chalky astringent drugs such as magnesium hydroxide and aluminum hydroxide, and making it easier to administer large amounts of high dosage medications such as calcium carbonate supplements. Antacids in a whip or aerosol foam become extremely palatable and easy to swallow making it possible to prepare products containing a much larger amount of active antacid ingredients so that greater effectiveness and compliance can be achieved than is common with conventional chewable antacid tablets or aqueous antacid suspensions. For example, a typical dose of magnesium hydroxide as a liquid laxative is 2 to 4 tablespoons, whereas the foam of the invention requires only 2 to 3 teaspoons to deliver the same amount of active ingredient. Similar desirable results can be achieved with antitussives such as dextromethorphan, antihistamines such as chlorpheniranime, decongestants such as pseudoephedrine and local anesthetics such as benzocaine or dyclonine.

The stability of the novel foam formulation enables it to be controlled in the sense that it can be measured on a spoon or a similar device for oral administraton, or measured into an applicator for rectal or vaginal administration. Obviously, such a foam is capable of being packaged in small, portable aerosol containers (the size of a typical breath spray container) which may be easily transported in a pocket or purse as well as in shaving cream-sized containers for home use.

The stability of the whip or foam product also enables the present invention to be utilized as a base for food products. Thus, it can be combined with numerous sweetening and flavoring agents to provide a whipped cream-type food product which needs no refrigeration and no preservatives. Sweetening and flavoring agents, of course, may also be employed to enhance the flavor of pharmaceutical products to further enhance the likelihood of patient compliance.

While not wishing to be limited to any particular theory, it is believed that the formulations of the present invention are capable of achieving the foregoing results without valve clogging due to a novel combination of ingredients that produces a high viscosity formulation capable of keeping the small solids particles dispersed and of lubricating the aerosol valve.

DESCRIPTION OF THE PREFERRED EMBODIMENTS

The foamable, edible anhydrous liquid oils utilized in the present invention are varied and of no great critical significance. Typical among the edible organic oils useful for the present invention are those such as soybean oil, partially hydrogenated soybean oil, linseed oil, corn oil, peanut oil, sunflower oil, cottonseed oil, olive oil, castor oil, liquid petrolatum, oleic acid, lauric acid, and mono- and diglyceride oils. As indicated above, the basic criteria for a liquid oil utilizable in the present invention is that it is foamable and edible.

Typically, the edible oils utilized in the present invention are present in the formulation in a percentage of 40 to 95% by weight of the total composition. A preferred range is 50 to 70% by weight of the total composition. The amount of oil may be varied based upon the nature and amount of the other ingredients in the formulation, such as the amount of dispersed solids. Ordinarily, the percentage amount of each other ingredient in the formulation is first selected and the oil is the ingredient added to bring the formulation to 100%.

Foaming agents utilizable in the present invention are selected from the group consisting of lecithin and various polyol fatty acid esters and mixtures thereof. Lecithin is the commercial name for a class of naturally occurring compounds derived from soybeans. These compounds are phosphatides and phospholipids. The principal components of lecithin are a naturally occurring mixture of phosphatidyl choline, phosphatidyl ethanolamine, inositol phosphitides and related phosphorous containing lipids. Chemically, lecithin is described as phosphatidyl choline and is a mixture of the diglycerides of stearic, palmitic and oleic acids linked to the choline ester of phosphoric acid. It is available commercially as a 60% solution in soybean oil or as a granular powder essentially free of soybean oil. A hydroxylated lecithin, modified to increase the hydrophilic properties is also commercially available. This hydroxylated lecithin is commonly supplied as a 60% solution in soybean oil.

The polyol fatty acid esters utilizable in the present invention are commercial products and are comprised of three types:

1. Glycerol esters of fatty acids.
2. Polyglycerol esters of fatty acids.
3. Sorbitan esters of fatty acids.

The glycerol esters which have been found to be advantageous in generating a suitable anhydrous edible aerosol foam are prepared by standard esterification methods and have an HLB of between 2.5 and 4.5.

Among the preferable glycerol fatty esters utilizable in the present invention are those such as glycerol monostearate (HLB 3.2) and glycerol monooleate (HLB 3.4).

The polyglycerol esters utilizable in the present invention are commercial products prepared by first polymerizing glycerine under alkaline conditions. The polymerization is controlled to yield the particular desired average molecular weight. Investigations indicate that the polymerization of glycerol progresses predominately in a straight-chain manner. The esters are prepared by reacting the polyglycerols with a specific fatty acid or by the alcoholysis of a triglyceride. By this method, it is possible to prepare esters ranging anywhere from hydrophilic monoesters such as decaglycerol monolaurate to a lipophilic decaglycerol decaoleate.

The polyglycerol esters preferably used in the present invention have an HLB value of between 4.0 and 13.0. These have been found to be most advantageous in generating a suitable anhydrous aerosol foam. Among the preferable polyglycerol esters utilizable in the present invention are those such as: hexaglycerol distearate (HLB 4.0), decaglycerol tetraoleate (HLB 6.0), triglycerol monostearate (HLB 7.0), triglycerol monooleate (HLB 7.0), octaglycerol monostearate (HLB 12.0) and octaglycerol monooleate (HLB 13.0).

The sorbitan fatty acid esters which have been found to be advantageous in generating a suitable anhydrous edible aerosol foam are commercial products prepared by standard esterification methods and have an HLB of between 3.0 and 7.0. Among the preferable sorbitan esters utilizable in the present invention are those such as sorbitan monostearate (HLB 4.7), sorbitan monooleate (HLB 4.3), and sorbitan mono palmitate (HLB 6.7).

Additionally, a combination of any of the polyol fatty acid esters may be utilized in the present invention.

The polyol fatty acid esters are somewhat more hydrophilic than lecithin so that their use allows the foamable, edible anhydrous liquid oil to be more easily dispersed when contacted with an aqueous medium. This gives a much less oily feel in the mouth and releases the suspended medicament more rapidly in the stomach. Additionally, they may be used in conjunction with lecithin in the same system which causes the lecithin to become more hydrophilic and therefore more palatable than the lecithin alone. This combination also causes the release of a suspended medicament faster in the stomach. As it is necessary for the final product to be edible, the polyol esters are approved for internal use by the Food and Drug Administration.

The foaming agent utilized in the present invention is present in an amount of from 2 to 40% by weight. The amount of foaming agent utilized depends upon the particular foaming agent being utilized, the particular foamable, edible, anhydrous liquid oil being utilized and the propellant system. A preferred range of foaming agent is from about 3 to 15% by weight of the composition, with 10% being especially preferred. It is a particularly desirable additional feature of the foaming agents that they possess surfactant properties and, therefore, affect the rate at which the insoluble solid active ingredient of the foam is released in the body. Accordingly, some variations in the amount of foaming agent in a particular formulation may be purposely chosen based on the nature of the solid active ingredient in order to control the rate of release.

The edible propellant can be selected from the class of hydrocarbons that are gaseous under atmospheric pressures and liquefy when compressed, or certain edible fluorocarbons such as FREON 115. The most commonly used are propane, butane and isobutane. Propane is approved for use in ingested products and can be obtained commercially in an odorless and tasteless form which is ideally suited for use in preparing the whip of the present invention. Since these liquefied gases are soluble in the oil vehicle of the composition, there is a resulting reduction in their vapor pressure. Therefore, it is most advantageous to use propane since it has the highest pressure of the three hydrocarbon propellants and, even when dissolved in the low concentrations normally employed in this invention, produces a product with a pressure of 30-40 pounds per square inch over atmospheric pressure. This pressure is required to eject the foam from the container and produce a stable, dense foam which can be measured onto a spoon to facilitate administration. However, since propane is soluble in the oil base, there is very little pressure drop from the first to the last actuation of the aerosol valve and a satisfactory foam is produced when each dose is expelled.

The amount of propellant used is critical since too much will produce an undesirable spray rather than the desired stable, measurable foam. Amounts of propellant in the range of from 1-10 wt. % are operative, but 3-5 wt. % is the preferred concentration based upon the total weight of the contents of the aerosol container. The amount of propellant used may vary somewhat, depending upon the nature and amount of the other ingredients in the composition but, in all cases, the lowest amount sufficient to form a stable, measurable foam without forming an unmeasurable spray will be selected.

Propellants other than the liquefied hydrocarbon gases can be used including compressed gases like nitrogen, nitrous oxide and carbon dioxide, but they do not produce the most desirable foams over the life of the product in use.

The edible anhydrous aerosol foam of the present invention may be used as a vehicle for any of a large variety of active pharmaceutical materials or cosmetic ingredients. Additionally, the foam itself can be used as a base for various sweetening and flavoring agents in order to provide a food item. The active pharmaceutical materials which can be incorporated in the foam of the present invention can be any of the common antacids, analgesics, antitussives, laxatives, calcium supplements, vitamins, minerals, or any other type of therapeutic agent.

A particularly important and surprising feature of the foams of this invention is their ability to suspend high concentrations, i.e., up to 50% by weight, of solids, and mask their taste upon ingestion of the foam. Preferably, the suspended particles are ground to a very fine particle size since this facilitates the formation and maintenance of a uniform dispersion and prevents clogging. Particle sizes in the range of 50 to 100 microns in diameter are preferred. Since the solid particles which comprise the active therapeutic ingredient are not normally soluble in the foam formulation, the drug is kept out of solution in the mouth as it is ingested. Thus, the need to mask the taste of bitter water soluble drugs such as acetaminophen, or smooth the taste of chalky astringent drugs such as magnesium hydroxide and aluminum hydroxide is markedly reduced. This greatly simplifies the formulation of such drugs and obviates any potential problems with absorption and side effects of other excipients. Additionally, the foam can incorporate flavoring agents to further enhance its taste.

The foam of the present invention can contain up to 50 wt. % of suspended solid particles without any appreciable valve malfunctioning, and will usually contain in excess of 15 wt. % of such solid particles since a primary purpose of the foam system is to deliver a high concentration of the active ingredient in the solid particles in a relatively small dose. This ability to suspend high percentages of solids without valve malfunctioning enables the aerosol foam system of the present invention to be utilized for a wide variety of formulations. The reasons for the unique ability of the foams to suspend such a high concentration of solids without valve clogging are not fully understood, but it is believed to result from a combination of the small particle size, the high viscosity of the foam formulation due to its low propellant content which aids in keeping the particles dispersed and reduces agglomeration and settling, and the lubricating effect of the oil on the valve.

The foams of the present invention are prepared by conventional formulating techniques. Thus, typically, the foamable edible anhydrous liquid oil and the foaming agent are mixed together along with any other soluble ingredients of the composition. The solid to be dispersed is then added and the resultant mixture passed through an appropriate mill to ensure uniform particle size. The batch is then submitted for aerosol filling to an aerosol can. An aerosol valve is placed on the can and the can is crimped. The food grade propellant is then added by pressure filling.

In addition to the active solid to be dispersed in the foam and the essential ingredients of the foam, there may also be incorporated in the foams of the present invention any of a variety of additives or a combination thereof, commonly added to aerosol compositions or to toiletries, cosmetics, or pharmaceuticals. Typically, such additives are those such as emollients, lubricants, humectants, abrasives, and perfumes.

It will be apparent to those skilled in the art that many modifications, both of materials and methods, may be practiced without departing from the purpose and intent of the disclosure.

EXAMPLE 1

Basic Foam System

| Lecithin, granular | 5.00% |
|---|---|
| Soybean Oil | 90.00 |
| Propane | 5.00 |
| | 100.00% |

Procedure: (All ingredients are by weight)

The lecithin and soybean oil are heated to 150° F. until all the lecithin is dissolved. The batch is cooled to room temperature and submitted for aerosol filling. The components are all soluble in the soybeam oil so that this foam does not require shaking. When the contents of the aerosol can are used, a copious foam is formed.

EXAMPLE 2

Antacid Foam

| Lecithin, granular | 5.000% |
|---|---|
| Glycerol Monostearate | 1.000 |
| Calcium Carbonate | 25.000 |
| Vanillin | 0.250 |

| | |
|---|---|
| Flavor | 0.100 |
| Sodium saccharin, fine powder | 0.025 |
| Soybean Oil | 65.625 |
| Propane | 3.000 |
| | 100.000% |

Procedure: (All ingredients are by weight)

Heat the lecithin, the glycerol monostearate and the soybeam oil to 150° F. until clear, add the vanillin and cool the batch to room temperature. Mix in the calcium carbonate, the sodium saccharin and the flavor. Pass the entire batch through an appropriate mill to ensure uniform particle size, Submit the batch for aerosol filling.

Because the active ingredients are in suspended form, the aerosol can must be shaken to ensure uniformity of the can. The glycerol monostearate is included for viscosity control. When the aerosol is used, a good tasting whippped cream-like product is obtained. Each heaping teaspoonful of foam (4 g.) will deliver 1.0 g. of active antacid.

EXAMPLE 3

Antacid Foam (30% Suspended Solids)

| | |
|---|---|
| Al(OH)$_3$, powdered gel | 10.00% |
| Mg(OH)$_2$, powdered | 10.00 |
| Sugar 12X, powdered | 10.00 |
| Lecithin, granular | 5.00 |
| Flavor, Mint | 0.10 |
| Soybean Oil, partially hydrogenated | 61.90 |
| Propane | 3.00 |
| | 100.00% |

Procedure: (All ingredients are by weight)

Heat the granular lecithin in the soybean oil to 160° F. until melted and clear. Cool to room temperature and mix in the Al(OH)$_3$, Mg(OH)$_2$, sugar and flavor. Stir until uniform. Pass resultant mixture through a homogenizer and fill into aerosol cans. Charge with propane.

EXAMPLE 4

Antacid Foam (30% Suspended Solids)

| | |
|---|---|
| Al(OH)$_3$ dried gel, powdered | 10.00% |
| Mg(OH)$_2$ fine powder | 10.00 |
| Lecithin, granular | 4.00 |
| Decaglycerol Tetraoleate | 3.00 |
| Powdered Sugar, 12X N.F. | 10.00 |
| Flavor, Mint | 0.10 |
| Soybean Oil, partially hydrogenated | 59.90 |
| Propane | 3.00 |
| | 100.00% |

Procedure: (All ingredients are by weight)

The lecithin and soybean oil are heated to 160° F. until clear and uniform. The batch is cooled to room temperature. The Al(OH)$_3$, Mg(OH)$_2$, sugar and flavor are stirred into the batch until uniform. The batch is then passed through a colloid mill and submitted for aerosol filling. Each heaping teaspoonful, 4.0 g., contains 400 mg. each of Al(OH)$_3$ and Mg(OH)$_2$.

EXAMPLE 5

Milk of Magnesia Foam (42% Suspended Solids)

| | |
|---|---|
| Mg(OH)$_2$ fine powder | 30.00% |
| Stearic Acid | 0.50 |
| Glycine, powdered | 1.00 |
| Lecithin, granular | 5.00 |
| Vanillin | 0.25 |
| Flavor, Mint | 0.10 |
| Sugar, 12X, powdered | 10.00 |
| Syloid 244 P, silica | 1.00 |
| Soybean Oil, partially hydrogenated | 49.15 |
| Propane | 3.00 |
| | 100.00% |

Procedure: (All ingredients are by weight) Heat the granular lecithin and stearic acid in the soybean oil to 160° F. until melted and clear to room temperature and stir in the Mg(OH)$_2$, glycine, vanillin, flavor, sugar and silica. Mix until uniform. Pass resultant mixture through a homogenizer and fill into aerosol cans. Charge with propane.

Each heaping teaspoonful of foam (4 g.) delivers 1.2 g. of Magnesium Hydroxide.

EXAMPLE 6

Milk of Magnesia (40 Suspended Solids)

| | |
|---|---|
| Decaglycerol Tetraoleate | 5.00% |
| Mg(OH)$_2$, powdered | 30.00 |
| Powdered sugar, 12X N.F. | 10.00 |
| Soybean Oil, partially hydrogenated | 52.00 |
| Propane | 3.00 |
| | 100.00% |

Procedure: (All ingredients are by weight)

The decaglycerol tetraoleate is mixed with the soybean oil until clear. The Mg(OH)$_2$ and the powdered sugar are than stirred into the batch. The dispersion is passed through a colloid mill and then submitted for aerosol filling.

Each heaping teaspoonful of foam (4 g.) delivers 1.2 g. of Mg(OH)$_2$.

EXAMPLE 7

Antitussive Foam

| | |
|---|---|
| Lecithin, granular | 5.000% |
| Glycerol monostearate | 2.500 |
| Vanillin | 0.250 |
| Sugar, fine powdered 10X | 25.000 |
| Flavor | 0.100 |
| Soybean Oil | 63.775 |
| Dextromethorphan HBr | 0.375 |
| Propane | 3.000 |
| | 100.000% |

Procedure: (All ingredients are by weight)

The lecithin, glycerol monostearate and soybeam oil are heated to 150° F. until clear and uniform. The vanillin is added and the batch cooled to room temperature. The sugar, flavor and dextromethorphan are added and mixed well. The entire batch is passed through a suitable mill to ensure uniform particle size. The batch is then submitted for aerosol filling. Because the active material and the sugar are in suspension, the aerosol can must be shaken before use. Each heaping teaspoonful (4 g.) will deliver 15 mg. of dextromethorphan as a good tasting whipped cream-like foam.

EXAMPLE 8

Antitussive Foam (30% Suspended Solids)

| | |
|---|---|
| Triglycerol monooleate | 5.000% |
| Powdered Sugar, 12X N.F. | 30.000 |
| Soybean Oil, partially hydrogenated | 61.525 |
| Mint Flavor | 0.100 |
| Dextromethorphan HBr | 0.375 |
| Propane | 3.000 |
| | 100.000% |

Procedure: (All ingredients are by weight)

The triglycerol monooleate is mixed with the soybean oil until clear and uniform. The powdered sugar and dextromethorphan HBr is stirred into the batch. The flavor is then added. The batch is passed through a colloid mill and then submitted to aerosol filling.

Each heaping teaspoonful of foam, 4 g., delivers 15 mg. of dextromethorphan HBr.

EXAMPLE 9

Calcium Supplement Foam (40% Suspended Solids)

| | |
|---|---|
| $CaCO_3$, fine powder U.S.P. | 30.00% |
| Powdered Sugar, 12X N.F. | 10.00 |
| Lecithin, granular | 4.00 |
| Decaglycerol tetraoleate | 2.00 |
| Flavor, Mint | 0.10 |
| Soybean Oil, partially hydrogenated | 50.90 |
| Propane | 3.00 |
| | 100.00% |

Procedure: (All ingredients are by weight)

The lecithin, granular is heated in the soybean oil at 160° F. until clear and uniform. The batch is cooled and the decaglycerol tetraoleate, $CaCO_3$, powdered sugar and flavor are mixed in and stirred until the batch is uniform. The batch is passed through a colloid mill and then submitted for aerosol filling. Each heaping teaspoonful of foam, 4.0 g., contains 1.2 g. of calcium carbonate.

EXAMPLE 10

Calcium Supplement Foam (41% Suspended Solids)

| | |
|---|---|
| $CaCO_3$, powdered | 30.00% |
| Sugar 12X, powdered | 10.00 |
| Glycine, powdered | 1.00 |
| Lecithin, granular | 5.00 |
| Vanillin | 0.25 |
| Flavor, Mint | 0.10 |
| Soybean Oil, partially hydrogenated | 50.65 |
| Propane | 3.00 |
| | 100.00% |

Procedure: (All ingredients are by weight)

Heat the granular lecithin in the soybean oil to 160° F. until melted and clear. Cool to room temperature and mix in the $CaCO_3$, sugar, glycine, vanillin and flavor. Stir until uniform. Pass resultant mixture thorugh a homogenizer and fill into aerosol cans. Charge with propane.

Each heaping teaspoonful of foam delivers 1.2 g. of calcium carbonate.

EXAMPLE 11

Children's Analgesic Foam

| | |
|---|---|
| Lecithin, granular | 5.00% |
| Glycerol Monostearate | 2.50 |
| Vanillin | 0.25 |
| Flavor | 0.10 |
| Sugar, fine powder 10X | 23.00 |
| Soybean Oil | 64.15 |
| Acetaminophen | 2.00 |
| Propane | 3.00 |
| | 100.00% |

Procedure: (All ingredients are by weight)

The lecithin, glycerol monostearate and soybean oil are heated to 150° F. until clear and uniform. The vanillin is added to the batch, cooled to room temperature. The sugar, flavor and acetaminophen are added and the batch mixed. The entire batch is then passed through a suitable mill to ensure a uniform particle size. The batch is then submitted for aerosol filling. Because the active ingredient and the sugar are suspended with the product, the aerosol can must be shaken before use.

Each heaping teaspoonful (4 g.) will deliver 80 mg. of acetaminophen in a good tasting whipped cream-like foam.

EXAMPLE 12

Chocolate Mousse Foam Food Topping

| | |
|---|---|
| Lecithin, granular | 5.00% |
| Sugar, fine powder 10X | 20.00 |
| Bakers chocolate | 4.00 |
| Glycerol monostearate | 2.50 |
| Vanillin | 0.25 |
| Flavor | 0.40 |
| Soybean Oil | 64.85 |
| Propane | 3.00 |
| | 100.00% |

Procedure: (All ingredients are by weight)

The lecithin, glycerol monostearate, and soybean oil are heated to 150° F. until clear and uniform. The vanillin and Bakers chocolate are mixed in and the batch cooled to room temperature. The sugar and flavor are added and the entire batch passed through a suitable mill to ensure particle uniformity. The batch is then submitted for aerosol filling. Because the sugar is suspended in the batch, the aerosol can must be shaken before use. When the contents are used, a good tasting whipped cream-like foam is formed.

EXAMPLE 13

Psyllium Bulk Laxative and Fiber Supplement

Utilizing the procedure of Example 10 and substituting powdered psyllium for the calcium carbonate, there is produced a psyllium foam which is suitable for use as a bulk laxative and fiber supplement.

EXAMPLE 14

Carrageenan Foam

Utilizing the ingredients and procedure of Example 10 with substitution of carrageenan for calcium carbonate provides a carrageenan foam suitable for use as an anti-ulcer treatment for gastrointestinal therapy.

EXAMPLE 15

Calcium Foam Whip

| | |
|---|---|
| Sorbitan monostearate | 2.00% |
| Glycerol monostearate | 2.00 |
| Decaglycerol tetraoleate | 5.00 |

| | |
|---|---|
| Calcium Carbonate | 30.00 |
| Sugar, powdered, 12x, NF | 10.00 |
| Cabosil M-5 | 1.00 |
| Flavor | 0.20 |
| Soybean Oil, partially hydrogenated | 46.80 |
| Propane | 3.00 |
| | 100.00% |

Prodedure: (All ingredients are by weight)

Heat the sorbitan monostearate, glycerol monostearate, glycerol monostearate, decaglycerol tetraoleate and soybeam oil to 60° C. Add the calcium carbonate, sugar, and cabosil M-5 with good mixing. Cool the mixture and add flavor. When the mixture is at room temperature, mill and submit for aerosol filling.

Each teaspoonful of foam (4.0 g.) delivers 1.2 g. of calcium carbonate.

EXAMPLE 16

Dextromethorphen Foam Whip

| | |
|---|---|
| Lecithin, granular | 5.00% |
| Sorbitan monostearate | 3.00 |
| Sugar, powdered, 12x, NF | 25.00 |
| Citric Acid | 0.10 |
| Cabosil M-5 | 0.50 |
| Dextromethorphen HBr | 0.25 |
| Flavor | 0.20 |
| Soybean Oil, partially hydrogenated | 62.90 |
| Aspartame | 0.05 |
| Propane | 3.00 |
| | 100.00% |

Procedure: (All ingredients by weight)

Heat the soybean oil, lecithin and sorbitan monostearate to 60°C. Add the sugar, citric acid, cabosil M-5, dextromethorphen HBr and aspartame with good mixing. Cool the mixture and add flavor. When the mixture is at room temperature, mill and submit for aerosol filling.

Each teaspoonful (3.0 g.) delivers 7.5 mg. of dextromethorphen HBr.

EXAMPLE 17

Trimethoprim Foam Whip (Urinary Drug)

| | |
|---|---|
| Trimethoprim | 1.30% |
| Lecithin, granular | 5.00 |
| Sorbitan monostearate | 4.00 |
| Veegum "F" (Magnesium, Aluminum Silicate) | 3.00 |
| Cabosil M-5 | 1.00 |
| Sugar, powdered, 12x, NF | 25.00 |
| Flavor | 0.20 |
| Soybean oil, partially hydrogenated | 57.50 |
| Propane | 3.00 |
| | 100.00% |

Procedure: (All ingredients are by weight)

Heat the lecithin, sorbitan monostearate and soybean oil to 60° C. Stir in the trimethoprim and veegum "F". Mix well. Cool the mixture to 50° C. and add the cabosil M-5 and the sugar. Continue cooling and add flavor. Mill the mixture and submit for aerosol filling.

Each teaspoonful (3.0 g.) delivers 40 mg. of trimethoprim.

EXAMPLE 18

Antacid Foam Whip

| | |
|---|---|
| Sorbitan monostearate | 4.00% |
| Decaglycerol tetraoleate | 6.00 |
| Magnesium Hydroxide, USP | 10.00 |
| Aluminum Hydroxide Dried Gel USP | 10.00 |
| Sugar, powdered, 12x, NF | 10.00 |
| Cabosil M-5 | 1.00 |
| Flavor | 0.20 |
| Soybean Oil, partially hydrogenated | 55.80 |
| Propane | 3.00 |
| | 100.00% |

Procedure: (All ingredients by weight)

Heat the sorbitan monostearate, decaglycerol tetraoleate and soybean oil to 60° C. Mix in the magnesium hydroxide, aluminum hydroxide dried gel, sugar, and cabosil N-5 with fast stirring. Cool the mixture and add flavor. Mill the mixture and submit for aerosol filling.

Each teaspoonful (4.0 g.) delivers 400 mg. each of magnesium hydroxide and aluminum hydroxide.

What is claimed is:

1. An edible, anhydrous aerosol foam composition comprising a foamable liquid oil, a foaming agent and a propellant, said propellant being present in an amount sufficient to produce a stable, measurable foam but insufficient to produce a spray when said composition is ejected through an aerosol valve, and dispersed solid particles, said particles comprising an active therapeutic agent.

2. The composition of claim 1 wherein said propellant comprises 1 to 10 wt. % of said composition.

3. The composition of claim 2 wherein said solid particles comprise at least 15 wt. % of said composition and said particles are insoluble in the other ingredients of said foam composition.

4. The composition of claim 3 wherein the average size of said solid particles is in the range of 50 to 100 microns.

5. The composition of claim 1 wherein said propellant comprises 1 to 10 wt. % of said composition, said foaming agent comprises 2 to 40 wt. % of said composition, said solid particles comprise at least 15 wt. % of said composition and are insoluble in the other ingredients of said foam composition and the balance of said composition is said liquid oil.

6. The composition of claim 5 wherein said propellant is a hydrocarbon.

7. The composition of claim 5 wherein said propellant is propane.

8. The composition of claim 5 wherein said liquid oil is selected from the group consisting of soybean oil, partially hydrogenated soybean oil, linseed oil, corn oil, peanut oil, sunflower oil, cottonseed oil, olive oil, castor oil, liquid petrolatums, oleic acid, lauric acid and mono- and diglyceride oils.

9. The composition of claim 5 wherein the foaming agent is selected from the group consisting of lecithin, polyglycerol esters of fatty acids having an HLB value of between 4.0 and 13.0, glycerol esters of fatty acids having an HLB value of between 2.5 and 4.5, sorbitan esters of fatty acids having an HLB value of between 3.0 and 7.0 and mixtures thereof.

10. The composition of claim 9 wherein said foaming agent comprises 2 to 40 wt. % of said composition.

11. The composition of claim 9 wherein the foaming agent is a mixture of lecithin and glycerol monostearate.

12. The composition of claim 9 wherein the foaming agent is a mixture of lecithin and decaglycerol tetraoleate.

13. The composition of claim 9 wherein the foaming agent is triglycerol monooleate.

14. The composition of claim 9 wherein the foaming agent is decaglycerol tetraoleate.

15. The composition of claim 9 wherein the foaming agent is sorbitan monostearate.

16. The composition of claim 9 wherein the foaming agent is a mixture of decaglycerol tetraoleate and sorbitan monostearate.

17. The composition of claim 9 wherein the foaming agent is a mixture of decaglycerol tetraoleate and glycerol monostearate.

18. The compositiion of claim 9 wherein the foaming agent is a mixutre of decaglycerol tetraoleate, sorbitan monostearate and glycerol monostearate.

19. The composition of claim 9 wherein the foaming agent is a mixture of sorbitan monostearate and glycerol monostearate.

20. The composition of claim 9 wherein the foaming agent is from about 3 to 15 wt. % of the composition.

21. The composition of claim 9 wherein the foaming agent is a mixture of lecithin, sorbitan monostearate and glycerol monostearate.

22. The composition of claim 9 wherein the foaming agent is a mixture of lecithin, sorbitan monostearate and decaglycerol tetraoleate.

23. The composition of claim 9 wherein the foaming agent is a mixture of lecithin and sorbitan monostearate.

* * * * *